United States Patent
Park et al.

(10) Patent No.: US 11,040,498 B2
(45) Date of Patent: Jun. 22, 2021

(54) MANUFACTURING DEVICE OF NERVE CONDUITS

(71) Applicant: RION CO., LTD., Gyeonggi-do (KR)

(72) Inventors: Ki Woong Park, Gyeonggi-do (KR); Ku Chan Chung, Gyeonggi-do (KR); Jung Keun Hyun, Seoul (KR); Jong Wan Kim, Chungcheongnam-do (KR)

(73) Assignee: RION CO., LTD., Gyeonggi-do (KR)

( * ) Notice: Subject to any disclaimer, the term of this patent is extended or adjusted under 35 U.S.C. 154(b) by 282 days.

(21) Appl. No.: 15/650,436

(22) Filed: Jul. 14, 2017

(65) Prior Publication Data

US 2018/0304553 A1    Oct. 25, 2018

(30) Foreign Application Priority Data

Apr. 24, 2017    (KR) .................... 10-2017-0052372

(51) Int. Cl.
| | | |
|---|---|---|
| *A61F 2/04* | (2013.01) | |
| *A61L 27/18* | (2006.01) | |
| *B29C 67/20* | (2006.01) | |
| *A61F 2/00* | (2006.01) | |
| *A61L 27/56* | (2006.01) | |
| *A61L 27/16* | (2006.01) | |
| *A61B 17/11* | (2006.01) | |
| *B29K 105/00* | (2006.01) | |
| *B29L 31/00* | (2006.01) | |

(Continued)

(52) U.S. Cl.
CPC ........ *B29C 67/202* (2013.01); *A61B 17/1128* (2013.01); *A61F 2/0077* (2013.01); *A61F 2/04* (2013.01); *A61L 27/16* (2013.01); *A61L 27/18* (2013.01); *A61L 27/56* (2013.01); *A61F 2002/0081* (2013.01); *A61F 2240/001* (2013.01); *A61L 2430/32* (2013.01); *B29K 2067/043* (2013.01); *B29K 2067/046* (2013.01); *B29K 2105/0073* (2013.01); *B29K 2105/0085* (2013.01); *B29K 2105/041* (2013.01); *B29L 2031/7532* (2013.01)

(58) Field of Classification Search
CPC ...... B29C 70/00; A61L 2430/32; A61L 27/56; A61B 17/1128; A61B 5/4041; A61B 5/4893; A61F 2/04; A61F 2002/0081; B29K 2105/041; B29K 2067/03
See application file for complete search history.

(56) References Cited

U.S. PATENT DOCUMENTS

| | | | |
|---|---|---|---|
| 2010/0076465 A1* | 3/2010 | Wiberg | A61B 17/1128 606/152 |
| 2016/0263784 A1* | 9/2016 | Itou | B29C 70/44 |
| 2017/0325933 A1* | 11/2017 | Liu | A61L 27/16 |

OTHER PUBLICATIONS

KR 2015-0105826 (Year: 2015).*

* cited by examiner

*Primary Examiner* — Marc C Howell
*Assistant Examiner* — Debjani Roy

(57) ABSTRACT

The present disclosure relates to an apparatus for manufacturing a nerve conduit, more particularly to an apparatus for manufacturing a porous nerve conduit using glass fibers whereby microchannels are formed using the space between the glass fibers and the defective rate and location-dependent variation of each nerve conduit can be minimized through uniform decompression during the manufacture. The nerve conduit manufactured according to the present disclosure can be manufactured to have various diameters and lengths to be applicable to in vitro and in vivo researches on nerves.

4 Claims, 8 Drawing Sheets

(51) Int. Cl.
*B29K 67/00* (2006.01)
*B29K 105/04* (2006.01)

Upper channels
Discontinuous
Lower channels

✓ Channel diameter : 16.54 ± 3.6 μm

✓ Number of channels : 7,777 ± 716.2

✓Small animal study & *in vitro* study        ✓Large animal study & *in vitro* study

MANUFACTURING DEVICE OF NERVE CONDUITS

CROSS-REFERENCE TO RELATED APPLICATION

This application claims priority of Korean Patent Application No. 10-2017-0052372, filed on Apr. 24, 2017, in the KIPO (Korean Intellectual Property Office), the disclosure of which is incorporated herein entirely by reference.

BACKGROUND OF THE INVENTION

Field of the Invention

The present disclosure relates to an apparatus for manufacturing a nerve conduit, and more particularly, to an apparatus for manufacturing a porous nerve conduit using glass fibers whereby microchannels are formed using the space between the glass fibers and the defective rate and location-dependent variation of each nerve conduit can be minimized through uniform decompression during the manufacture.

Description of the Related Art

When a peripheral nerve is damaged due to injury, the sections of the cut nerve are connected with each other directly. However, such anastomosis is almost impossible for most nerves and, in this case, autogenous nerve grafting is conducted to restore its function. However, the autogenous nerve grafting is problematic in that it is difficult to match the thickness and shape of the nerve tissue of the damaged area and the grafted nerve tissue, the nerves that can be taken for the grafting are limited and the decline in function can occur at the area where the grafted nerve is taken. Therefore, a nerve conduit is used to restore the function of a damaged nerve.

The nerve conduit connects both ends of the damaged nerve and serves as a means of guiding nerve regeneration. The both ends of the damaged nerve are fixed inside the nerve conduit to induce the connection of the nerve in the conduit. When the nerve conduit is used, it is advantageous in that the infiltration of scar tissue interfering with nerve regeneration can be prevented, nerve regeneration can be induced along a desired direction, the nerve regeneration promoting substances secreted from the nerve itself is maintained inside the conduit and the substances interfering with the regeneration can be blocked.

The nerve conduit should be biocompatible to avoid tissue rejection and should be biodegraded after nerve regeneration so that the removal of the nerve conduit is unnecessary after the nerve regeneration. Also, the degradation product of the nerve conduit should be nontoxic in the body. In addition, the nerve conduit should have the mechanical property to maintain the inside space during the nerve regeneration, should have suitable flexibility and tensile strength so that the end portion of the nerve conduit can be maintained stably after the insertion of the nerve conduit, should be able to prevent damage to nearby normal tissues and should be easily transplantable. As the material of the nerve conduit, natural polymers (collagen, chitosan, etc.) and synthetic polymers (silicone, polylactic acid (PLA), polyglycolic acid (PGA), poly(lactic acid-co-glycolic acid) (PLGA), polycaprolactone, etc.) are being studied.

Among them, collagen is the most frequently used natural polymer material. Collagen has been frequently used as the material of the nerve conduit for nerve regeneration due to excellent biocompatibility and weak antigenicity. However, the use of collagen is problematic in that it has to be extracted from an animal and large-scale production is difficult because its storage is complicated. In addition, it is limited in clinical application because of high cost and its tensile strength is very weak in vivo. The nerve conduit based on synthetic polymers such as polylactic acid, poly (lactic acid-co-glycolic acid), etc. with proven biocompatibility has superior structural stability and tensile strength because it is formed of a polymer tube without pores. However, it is problematic in that the control of physical properties is difficult and the exchange of body fluid is not achieved easily.

Although the inventors of the present disclosure have disclosed a nerve conduit using glass fibers in Korean Patent Application No. 10-2014-0027854 to solve these problems. However, the difficulty in the exchange of body fluid has not been solved.

SUMMARY OF THE INVENTION

The present disclosure is directed to providing an apparatus for manufacturing a porous nerve conduit having microchannels and micropores together.

The present disclosure is also directed to providing an apparatus for manufacturing a porous nerve conduit using glass fibers whereby microchannels are formed using the space between the glass fibers.

The present disclosure is also directed to providing a porous nerve conduit manufactured by the apparatus of the present disclosure.

In a first aspect, the present disclosure provides an apparatus for manufacturing a porous nerve conduit using glass fibers, including: (a) a container which has upper channels and lower channels and in which a plurality of glass fibers are inserted; (b) a polymer material injection means which injects a polymer material into the container; and (c) a vacuum application means which applies vacuum to the inside of the container, wherein the vacuum application means includes: (i) a vacuum pump which is connected to a vacuum tank and applies vacuum to the inside of the vacuum tank; (ii) the vacuum tank which is connected to the vacuum pump at one side and the inside of which is maintained at vacuum; (iii) a distribution vacuum controller which connects the other side of the vacuum tank to the inside of a chamber and applies vacuum to the inside of the container; and (iv) a vacuum chamber which is connected to the distribution vacuum controller and includes the container and the injection means inside thereof.

The distribution vacuum controller may include 1-100 air valve(s), a regulator and 2-100 vacuum control means including 1-100 vacuum release valve(s).

The lower channel may have a smaller diameter than the upper channel and the container may be sloped with a discontinuous angle.

The container may be formed of a transparent material so that the infiltration of the polymer solution can be checked visually.

In a second aspect, the present disclosure provides a method for manufacturing a porous nerve conduit using the apparatus for manufacturing a nerve conduit, including: (a) a step of inserting a plurality of glass fibers into a container having upper and lower channels; (b) a step of injecting a polymer material into the container having the plurality of glass fibers inserted; (c) a step of infiltrating the polymer material between the glass fibers by applying vacuum from the channels; (d) a step of separating the glass fibers from the container; and (e) a step of dissolving the glass fibers by immersing the separated glass fibers in water, wherein the step (c) includes: (i) a step of forming vacuum inside a vacuum tank using a vacuum pump; (ii) a step of decompressing the inside of a chamber by moving air inside a vacuum chamber to the vacuum tank using an air valve of a distribution vacuum controller and infiltrating the polymer material between the glass fibers; and (iii) a step of restoring the inside of the chamber to normal pressure using a vacuum release valve after the infiltration of the polymer material between the glass fibers has been completed.

The polymer material may contain: one or more selected from a group consisting of collagen, gelatin, chitosan, alginate, hyaluronic acid, dextran, silk, cellulose, poly-3-hydroxybutyrate (PHB), polyhydroxyvalerate (PHV), poly(hydroxybutyrate-co-valerate) (PHBV), polyorthoester, polyvinyl alcohol (PVA), polyethylene glycol (PEG), polyurethane, polyacrylic acid, poly(N-isopropylacrylamide), a poly(ethylene oxide)-poly(propylene oxide)-poly(ethylene oxide) copolymer, poly(dioxanone-b-caprolactone), poly($\varepsilon$-caprolactone) (PCL), poly(lactic acid) (PLA), poly-L-lactide (PLLA), poly-D-lactide (PDLA), poly-D,L-lactide (PDLLA), poly(glycolic acid) (PGA) or poly(lactic acid-co-glycolic acid) (PLGA) as a polymer; and one or more selected from a group consisting of methylene chloride (dichloromethane, DCM), 1,4-dioxane, chloroform, acetone, anisole, ethyl acetate, methyl acetate, N-methyl-2-pyrrolidone, hexafluoroisopropanol (HFIP), tetrahydrofuran (THF), dimethyl sulfoxide (DMSO), 2-pyrrolidone, triethyl citrate, trifluoroacetic acid (TFA), dimethylformamide (DMF), ethyl lactate, propylene carbonate, benzyl alcohol, benzyl benzoate, Miglyol 810, isopropanol, ethanol, acetonitrile or tetraglycol (TG) as a solvent.

The weight/volume % (w/v %) of the polymer and the solvent may be 10-40%.

Pores may be formed in the polymer as the solvent is separated from the polymer as it is phase-separated from the water during the step of immersing in the water.

The polymer material may be in a solution state at room temperature.

The method for manufacturing a porous nerve conduit using glass fibers may further include: a step of cooling a nerve conduit formed after the step of dissolving the glass fibers with liquid nitrogen; and a step of shaping the cooled nerve conduit by cutting.

The application of vacuum may be repeated multiple times.

In a third aspect, the present disclosure provides a porous nerve conduit manufactured by the manufacturing method.

Microchannels may be formed along the axis direction of the nerve conduit as glass fibers are inserted into a container along the axis direction.

Micropores may be formed in the nerve conduit as a solvent is dissolved in water.

The present disclosure provides the following effects.

By infiltrating a mixture of the hydrophobic polymer poly(lactic acid-co-glycolic acid) (PLGA) and the hydrophobic solvent tetraglycol (TG) between glass fibers and immersing the same in water, the hydrophobic tetraglycol (TG) is physically separated from the polymer constituting a nerve conduit and, as a result, micropores allowing body fluid exchange can be formed.

As the poly(lactic acid-co-glycolic acid) (PLGA) is mixed with the tetraglycol (TG), the melting point of the polymer solution is decreased. As the PLGA is dissolved with the TG and then maintained in a solution state at room temperature, the polymer material may be used without a process of dissolving again.

By infiltrating the polymer solution with a predetermined viscosity into the space between the glass fibers and repeatedly applying vacuum multiple times, a nerve conduit with a uniform density can be manufactured.

BRIEF DESCRIPTION OF THE DRAWINGS

The above and other features and advantages will become more apparent to those of ordinary skill in the art by describing in detail exemplary embodiments with reference to the attached drawings, in which.

DETAILED DESCRIPTION

Figure 1:
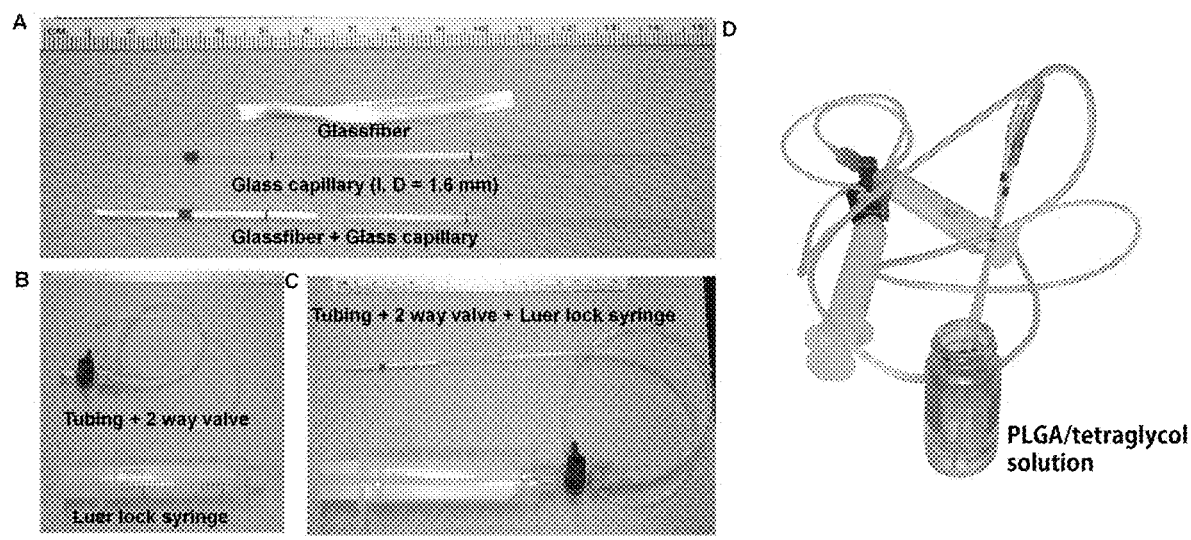
FIG. 1 shows photographs illustrating a method for manufacturing a porous nerve conduit. A shows glass fibers, a glass capillary and a glass capillary into which glass fibers are inserted, B shows a silicone tube coupled with a 2-way valve and a Luer lock syringe, C shows a silicone tube coupled with a 2-way valve and a Luer lock syringe, and D shows application of vacuum into a glass tube using a syringe.

The present invention now will be described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "includes", "comprises" and/or "comprising," when used in this specification, specify the presence of stated features, integers, steps, operations, elements, and/or components, but do not preclude the presence or addition of one or more other features, integers, steps, operations, elements, components, and/or groups thereof. In addition, a term such as a "unit", a "module", a "block" or like, when used in the specification, represents a unit that processes at least one function or operation, and the unit or the like may be implemented by hardware or software or a combination of hardware and software.

Reference herein to a layer formed "on" a substrate or other layer refers to a layer formed directly on top of the substrate or other layer or to an intermediate layer or intermediate layers formed on the substrate or other layer. It will also be understood by those skilled in the art that structures or shapes that are "adjacent" to other structures or shapes may have portions that overlap or are disposed below the adjacent features.

In this specification, the relative terms, such as "below", "above", "upper", "lower", "horizontal", and "vertical", may be used to describe the relationship of one component, layer, or region to another component, layer, or region, as shown in the accompanying drawings. It is to be understood that these terms are intended to encompass not only the directions indicated in the figures, but also the other directions of the elements.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Preferred embodiments will now be described more fully hereinafter with reference to the accompanying drawings. However, they may be embodied in different forms and should not be construed as limited to the embodiments set forth herein. Rather, these embodiments are provided so that this disclosure will be thorough and complete, and will fully convey the scope of the disclosure to those skilled in the art.

The present disclosure relates to an apparatus for manufacturing a porous nerve conduit using glass fibers, including: (a) a container which has upper channels and lower channels and in which a plurality of glass fibers are inserted; (b) a polymer material injection means which injects a polymer material into the container; and (c) a vacuum application means which applies vacuum to the inside of the container, wherein the vacuum application means includes: (i) a vacuum pump which is connected to a vacuum tank and applies vacuum to the inside of the vacuum tank; (ii) the vacuum tank which is connected to the vacuum pump at one side and the inside of which is maintained at vacuum; (iii) a distribution vacuum controller which connects the other side of the vacuum tank to the inside of a chamber and applies vacuum to the inside of the container; and (iv) a vacuum chamber which is connected to the distribution vacuum controller and includes the container and the injection means inside thereof.

The present disclosure also relates to a method for manufacturing a porous nerve conduit using the apparatus for manufacturing a nerve conduit, including: (a) a step of inserting a plurality of glass fibers into a container having upper and lower channels; (b) a step of injecting a polymer material into the container having the plurality of glass fibers inserted; (c) a step of infiltrating the polymer material between the glass fibers by applying vacuum from the channels; (d) a step of separating the glass fibers from the container; and (e) a step of dissolving the glass fibers by immersing the separated glass fibers in water, wherein the step (c) includes: (i) a step of forming vacuum inside a vacuum tank using a vacuum pump; (ii) a step of decompressing the inside of a chamber by moving air inside a vacuum chamber to the vacuum tank using an air valve of a distribution vacuum controller and infiltrating the polymer material between the glass fibers; and (iii) a step of restoring the inside of the chamber to normal pressure using a vacuum release valve after the infiltration of the polymer material between the glass fibers has been completed.

The term "polymer material" refers to one obtained by dissolving a hydrophobic polymer in a hydrophobic solvent. In the present disclosure, one or more selected from a group consisting of collagen, gelatin, chitosan, alginate, hyaluronic acid, dextran, silk, cellulose, poly-3-hydroxybutyrate (PHB), polyhydroxyvalerate (PHV), poly(hydroxybutyrate-co-valerate) (PHBV), polyorthoester, polyvinyl alcohol (PVA), polyethylene glycol (PEG), polyurethane, polyacrylic acid, poly(N-isopropylacrylamide), a poly(ethylene oxide)-poly(propylene oxide)-poly(ethylene oxide) copolymer, poly(dioxanone-b-caprolactone), poly(ε-caprolactone) (PCL), poly(lactic acid) (PLA), poly-L-lactide (PLLA), poly-D-lactide (PDLA), poly-D,L-lactide (PDLLA), poly (glycolic acid) (PGA) or poly(lactic acid-co-glycolic acid) (PLGA) may be used as the hydrophobic polymer and one or more selected from a group consisting of methylene chloride (dichloromethane, DCM), 1,4-dioxane, chloroform, acetone, anisole, ethyl acetate, methyl acetate, N-methyl-2-pyrrolidone, hexafluoroisopropanol (HFIP), tetrahydrofuran (THF), dimethyl sulfoxide (DMSO), 2-pyrrolidone, triethyl citrate, trifluoroacetic acid (TFA), dimethylformamide (DMF), ethyl lactate, propylene carbonate, benzyl alcohol, benzyl benzoate, Miglyol 810, isopropanol, ethanol, acetonitrile or tetraglycol (TG) may be used as the hydrophobic solvent. Specifically, the polymer material refers to a PLGA-TG solution prepared using PLGA as the polymer and TG as the solvent.

The hydrophobic polymer may be poly(lactic acid-co-glycolic acid) (PLGA) and the hydrophobic solvent may be tetraglycol (TG). According to the present disclosure, because the PLGA is dissolved with the TG and then maintained in a solution state at room temperature, the polymer material may be used without a process of dissolving again.

The weight/volume % (w/v %) of the polymer and the solvent refers to the weight (g) of the polymer dissolved in 1 L of the solvent. The weight/volume % (w/v %) may be 10-40%, more specifically 15-25%, most specifically 20%. If the weight/volume % is smaller than the above-described range, porosity may increase greatly due to the excessive use of the solvent. In the opposite case, enough pores may not be formed.

The vacuum application means may include (i) a vacuum pump which is connected to a vacuum tank and applies vacuum to the inside of the vacuum tank; (ii) the vacuum tank which is connected to the vacuum pump at one side and the inside of which is maintained at vacuum; (iii) a distribution vacuum controller which connects the other side of the vacuum tank to the inside of a chamber and applies vacuum to the inside of the container; and (iv) a vacuum chamber which is connected to the distribution vacuum controller and includes the container and the injection means inside thereof and the step (c) may include: (i) a step of forming vacuum inside a vacuum tank 400 using a vacuum pump 200; (ii) a step of decompressing the inside of a chamber by moving air inside a vacuum chamber to the vacuum tank using an air valve 112 of a distribution vacuum controller 100 and infiltrating the polymer material between the glass fibers; and (iii) a step of restoring the inside of the chamber to normal pressure using a vacuum release valve 113 after the infiltration of the polymer material between the glass fibers has been completed. If the inside of the chamber is decompressed using an existing vacuum pump, it is difficult to compress the inside of the chamber at a constant speed and it is difficult to form uniform pores in the porous nerve conduit because the pressure near the portion connected to the conduit decreases faster than the portion far from the conduit. In particular, because the polymer material is infiltrated between the glass fibers through decompression in the present disclosure, it is highly likely that defects may occur in the nerve conduit is when constant pressure is not formed. Accordingly, it is desired that the inside of the chamber is decompressed at a constant speed using the vacuum tank 400 such that the inside of the chamber has a constant pressure using the distribution vacuum controller 100. More specifically, the distribution vacuum controller 100 may include 1-100 air valve(s) 112, a regulator 111 and 2-100 distribution vacuum control means 110 including 1-100 vacuum release valve(s) 113. In addition, for automated production of the nerve conduit, each of the vacuum pump, the vacuum tank, the chamber and the distribution vacuum controller may be equipped with a pressure sensor and a control means and a valve may be equipped at a conduit connecting each component, such that the inside of the chamber is automatically maintained at a constant pressure.

The lower channel may have a smaller diameter than the upper channel, such that the glass fibers injected into the container remain filled in the container without flowing out.

The container may be sloped with a discontinuous angle. More specifically, the container may have upper and lower channels formed to be sloped with a discontinuous angle, although not being limited thereto.

Due to the container sloped with a discontinuous angle and the upper and lower channels thereof, the inserted glass fibers have constant intervals and the microchannels in the space where the glass fibers have been dissolved also have constant intervals. That is to say, because the porous nerve conduit manufactured according to the present disclosure has microchannels formed with constant intervals, nerve regeneration can be induced along the same direction.

The upper channels and the lower channels of the container may be formed by heating the center portion of the glass tubes and thereby forming a bottleneck, although not being limited thereto.

The polymer material may be in a solution state at room temperature.

The method for manufacturing a porous nerve conduit using glass fibers may further include: a step of cooling a nerve conduit formed after the step of dissolving the glass fibers with liquid nitrogen; and a step of shaping the cooled nerve conduit by cutting.

The container may be formed of a transparent material so that the infiltration of the polymer solution can be checked visually. Specifically, it may be formed of glass, although not being limited thereto.

The application of vacuum may be repeated multiple times. Through this, a nerve conduit with a uniform density may be manufactured.

The present disclosure also provides a porous nerve conduit manufactured according to the manufacturing method of the present disclosure.

Microchannels may be formed along the axis direction of the nerve conduit as glass fibers are inserted into a container along the axis direction. More specifically, by inserting the glass fibers into the upper channels of the container (glass tube) along the axis direction, injecting a polymer material (PLGA-TG solution) into the container and infiltrating into the glass fibers by applying vacuum and then dissolving out the glass fibers by separating from the container and immersing in water (DW), microchannels formed of a hydrophobic polymer (PLGA) may be formed in the space where the glass fibers have been dissolved. That is to say, a nerve conduit having microchannels formed in the axis direction may be formed in the space where the glass fibers have been dissolved by inserting the glass fibers along the axis direction of the container and then dissolving the glass fibers.

The term "microchannel" refers to a void space of a size of 10-20 μm formed in the space where the glass fibers have been dissolved.

Micropores may be formed in the nerve conduit as a solvent is dissolved in water. More specifically, the micropores may be formed inside the microchannels as the glass fibers infiltrated with the polymer material (PLGA-TG solution) are released from the nerve conduit as TG reacts (dissolution) with water (DW) as they are immersed in the water (DW). In the present disclosure, the dissolution means the separation of the TG from the polymer material.

Figure 8:
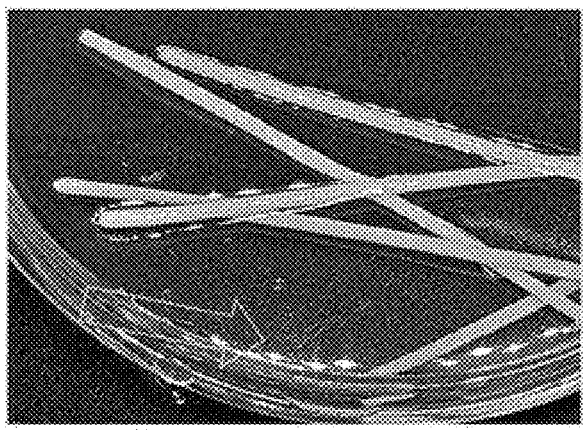
FIG. 8 shows TG released from a porous nerve conduit and submerged in DW; yellow arrow: TG.
Figure 8:
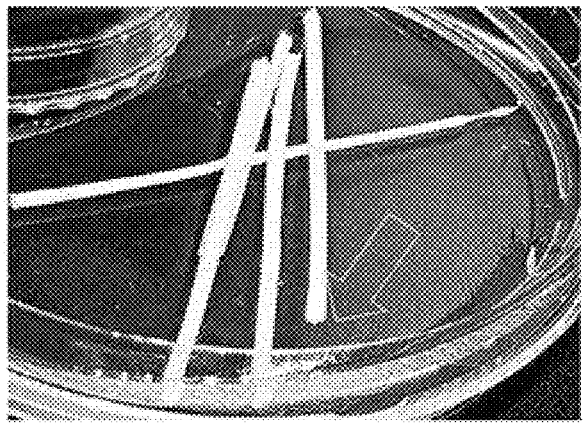
Figure 8:
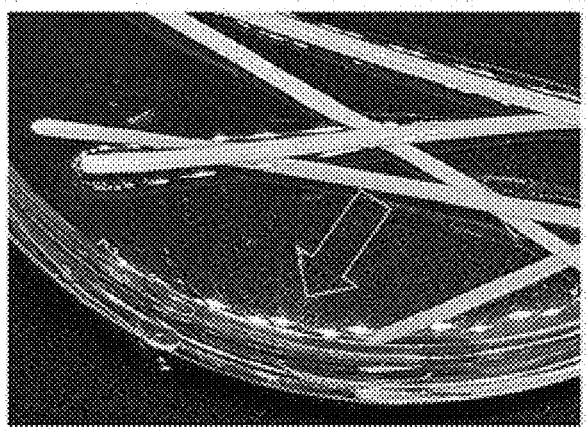
Figure 8:
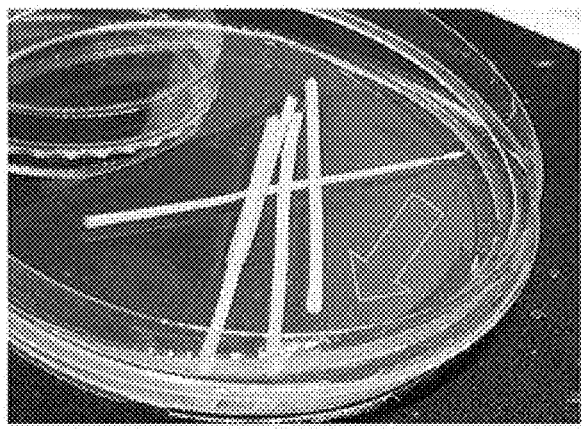
Figure 8:
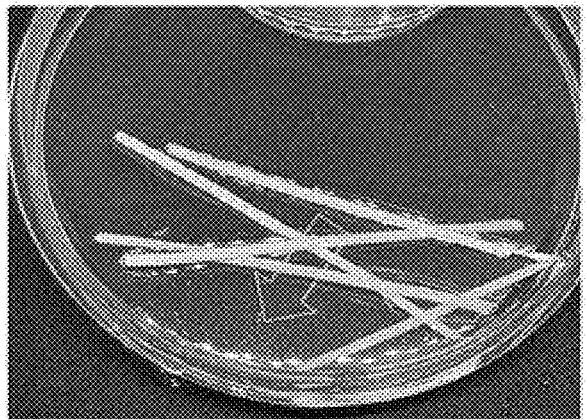

The term "micropores" refers to fine pores formed in the microchannels as the solvent is dissolved in DW and released from the nerve conduit. The nerve conduit manufactured according to the present disclosure allows easy body fluid exchange due to the microchannels. Because the solvent released from the nerve conduit has a higher density (1.09 g/mL) than DW, it is submerged like heat haze in the DW (FIG. 8).

The porous nerve conduit manufactured according to the present disclosure can be manufactured to have various diameters and lengths. The diameters and lengths may be varied freely to be applicable to in vitro and in vivo researches on nerves.

Hereinafter, the present disclosure will be described in detail through examples. However, the following examples are for illustrative purposes only and the scope of the present disclosure is not limited by the examples. The following examples are provided for better understanding of the present disclosure by those of ordinary skill in the art.

<Example 1> Manufacturing of Porous Nerve Conduit Using Glass Fibers 1

A 20% (w/v) PLGA-TG solution (polymer material) was prepared by mixing the hydrophobic polymer poly(lactic acid-co-glycolic acid) (PLGA) (lactic acid/glycolic acid mol %, 85:15) and the hydrophobic solvent tetraglycol (TG) (density: 1.09 g/mL, Sigma-Aldrich, USA) at a weight/volume (w/v) ratio of 20% (w/v) and then dissolving at 60° C. for 18 hours.

A glass capillary with an inner diameter of 1.6 mm and a length of 13 cm was heated at the center portion to form a bottleneck, thereby forming upper and lower channels sloped with a discontinuous angle. The lower channels were formed to have smaller diameters than the upper channel. Then, 7000-8500 strands of a water-soluble glass fiber ($50P_2O_5$-$20CaO$-$30Na_2O$ in mol % (1100° C., 800 rpm)) with diameters of 10-20 μm were cut to 5-6 cm and inserted densely into the upper channels of the glass tube along the axis direction (FIG. 1A and FIG. 2A).

A pressure device prepared by connecting a Luer lock syringe equipped with a silicone tube of an inner diameter of 0.8 mm and a length of 15 cm, coupled with a 2-way valve, to the upper channels of the glass fiber-inserted glass tube (FIG. 1B and FIG. 1C).

Figure 2:
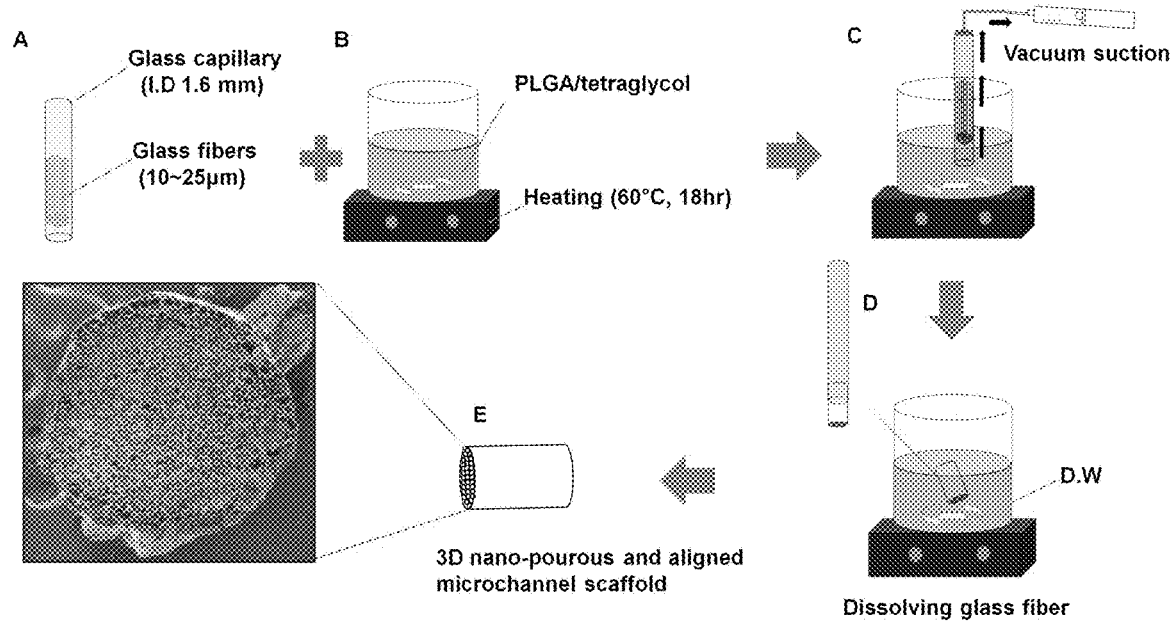
FIG. 2 schematically shows a method for manufacturing a porous nerve conduit.

After immersing the lower channels of the glass tube in a 20% (w/v) PLGA-TG solution at room temperature, vacuum was repeatedly applied into the glass tube using a syringe such that the 20% (w/v) PLGA-TG solution was completely infiltrated into the void space between the glass fibers (FIG. 1D and FIG. 2C).

Figure 3:
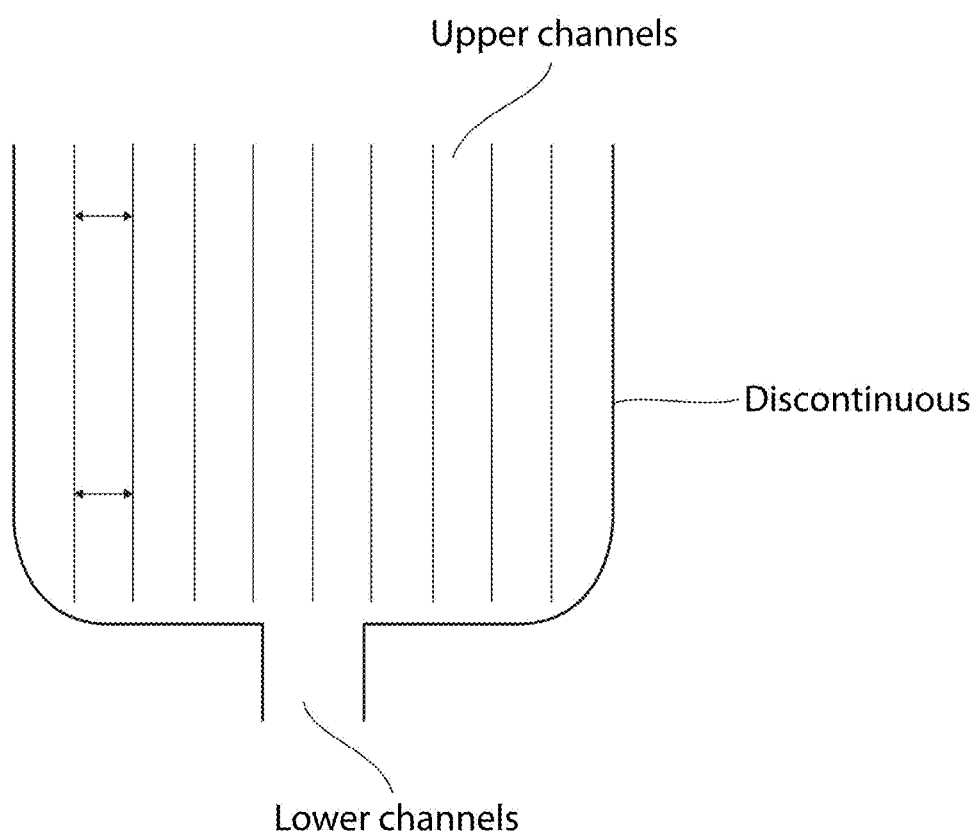
FIG. 3 and FIG. 4 shows channel formation in a container with a discontinuous or continuous slope.
Figure 4:
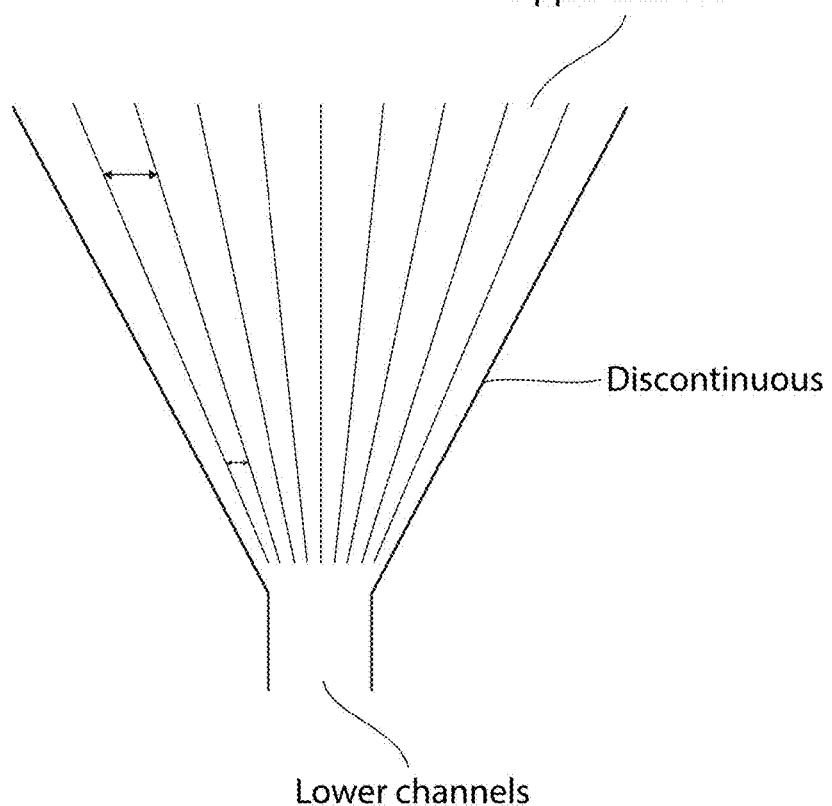

In this example, the diameter of the lower channels was decreased than that of the upper channels with a discontinuous angle as shown in FIG. 3. If the angle is continuous (FIG. 4), it is difficult to maintain constant intervals between the glass fibers because the intervals between the glass fibers decrease gradually. If the intervals between the glass fibers are not constant, the direction of nerve regeneration induced by the glass fibers becomes different depending on the channels. As a result, it is difficult to induce nerve regeneration in the same direction.

Figure 5:
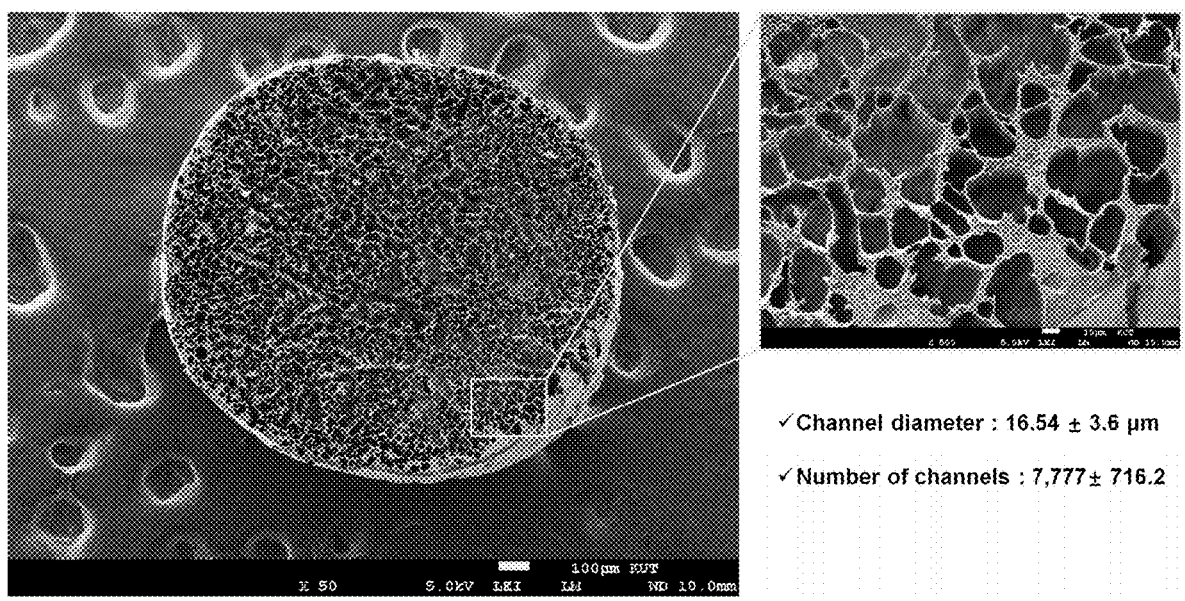
FIG. 5 shows a transverse cross-sectional SEM image of a porous nerve conduit; scale bar=(left) 100 μm, (right) 10 μm.
Figure 6:
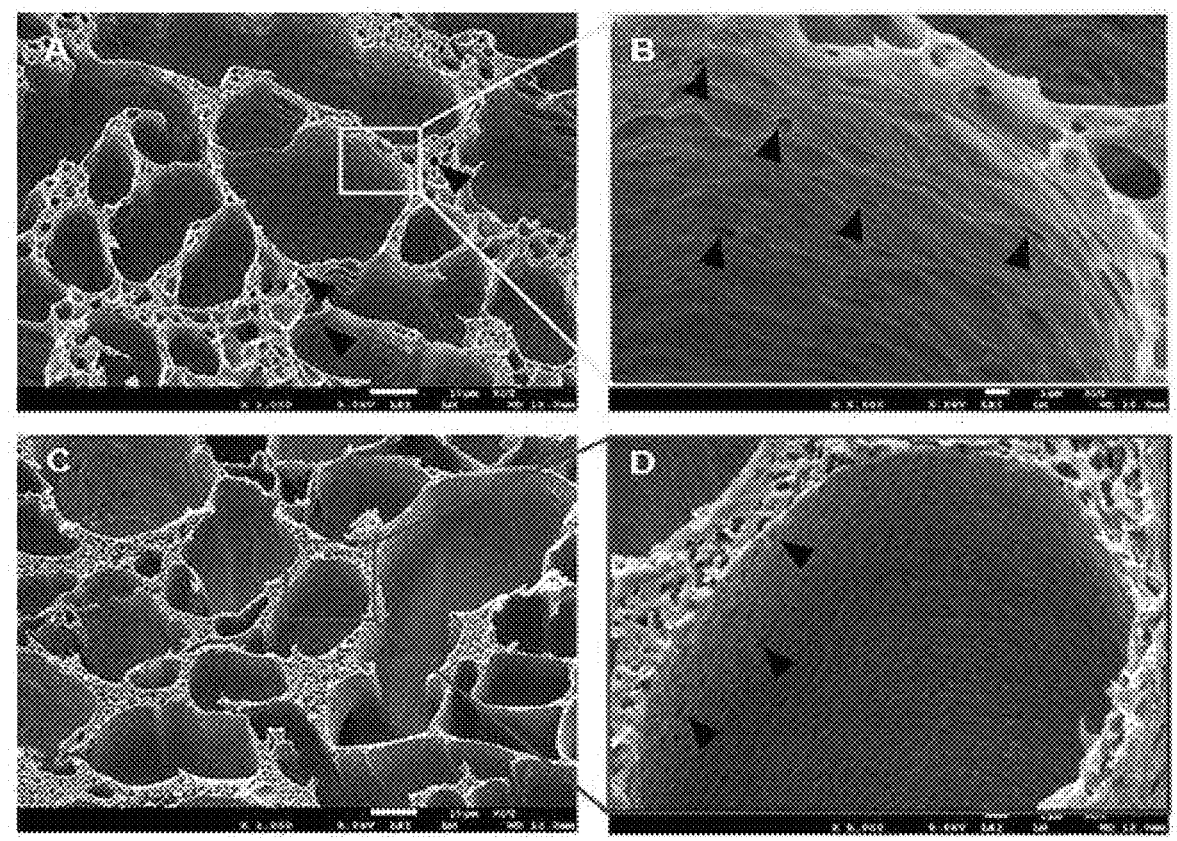
FIG. 6 shows magnified SEM images showing a microstructure at the transverse cross section of a porous nerve conduit; scale bar=(A, C) 10 μm, (B, D) 1 μm, ▶=micropores inside channel.
Figure 7:
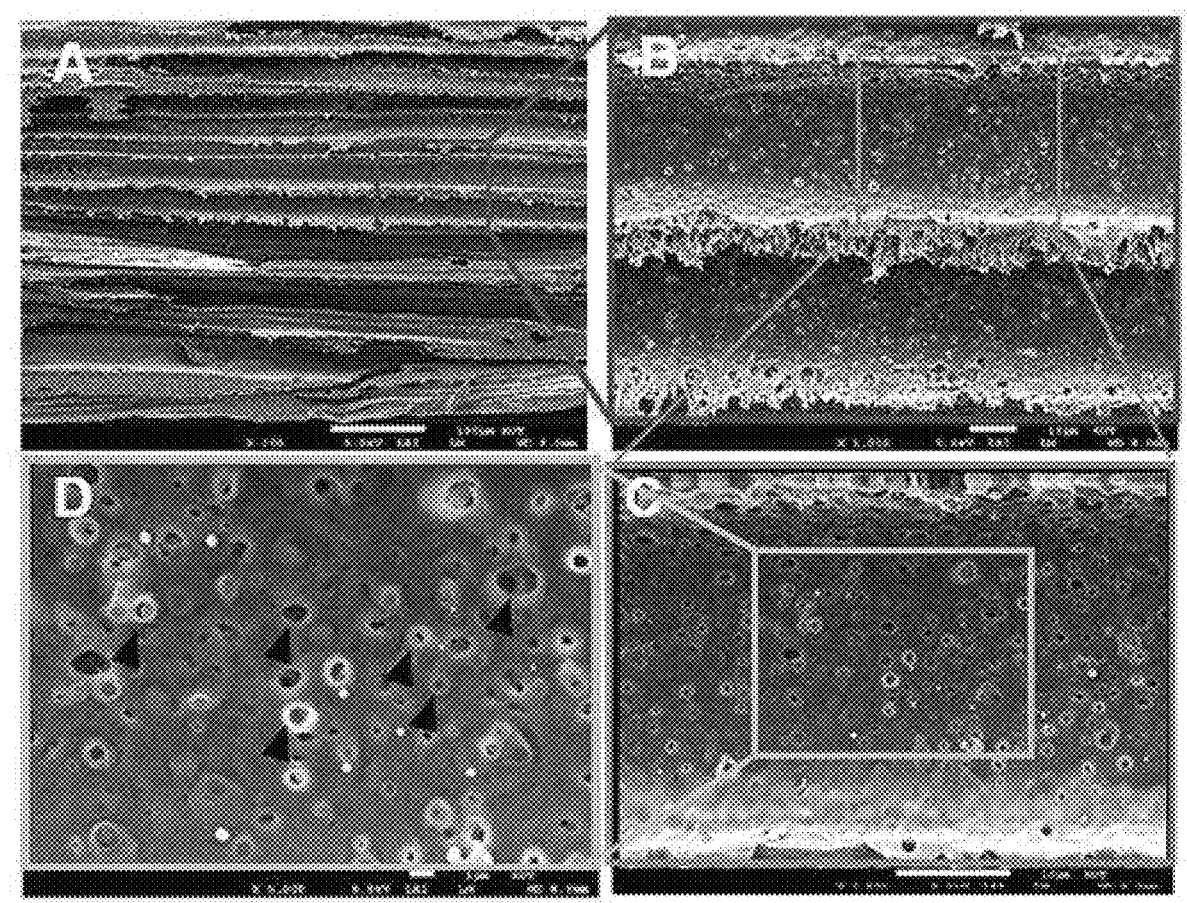
FIG. 7 shows longitudinal cross-sectional SEM images of a porous nerve conduit; scale bar=(A) 100 μm, (B) 10 μm, (C) 10 μm, (D) 1 μm.

The PLGA-TG solution-infiltrated glass fibers were separated from the glass tube using a wire with a diameter of 1.5 mm and a length of 15 cm and, immediately thereafter, completely immersed in ultrapure water (distilled water, DW) at 10-20° C. for at least 24 hours (FIG. 2D), so that the glass fibers were completely dissolved and about 7,000-8,500 (7,777±716.2) microchannels of PLGA, with diameters of 10-20 μm (16.54±3.6 μm), were formed in the space where the glass fibers had been dissolved (FIG. 2E and FIG. 5). The microchannels were formed as the glass fibers were dissolved in DW at 10-20° C. and PLGA was hardened at the same time. Also, micropores were formed inside the microchannels as the glass fibers infiltrated with the PLGA-TG solution were as TG reacted (dissolution) with DW while they were immersed in DW (FIG. 5, FIG. 6 and FIG. 7). Because the solvent released from the nerve conduit had a higher density than DW, it was submerged like heat haze in the DW (FIG. 8).

Figure 9:
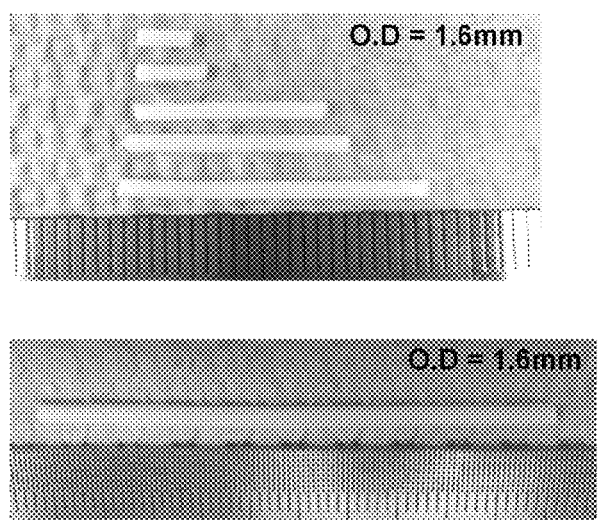
FIG. 9 shows porous nerve conduits manufactured with various diameters and lengths depending on applications.
Figure 9:
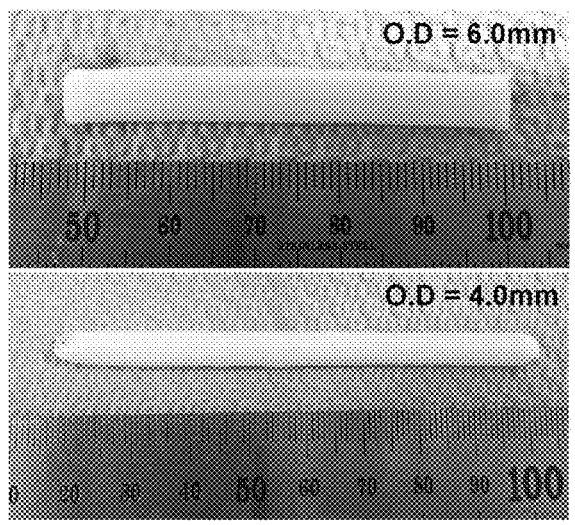
Figure 10:
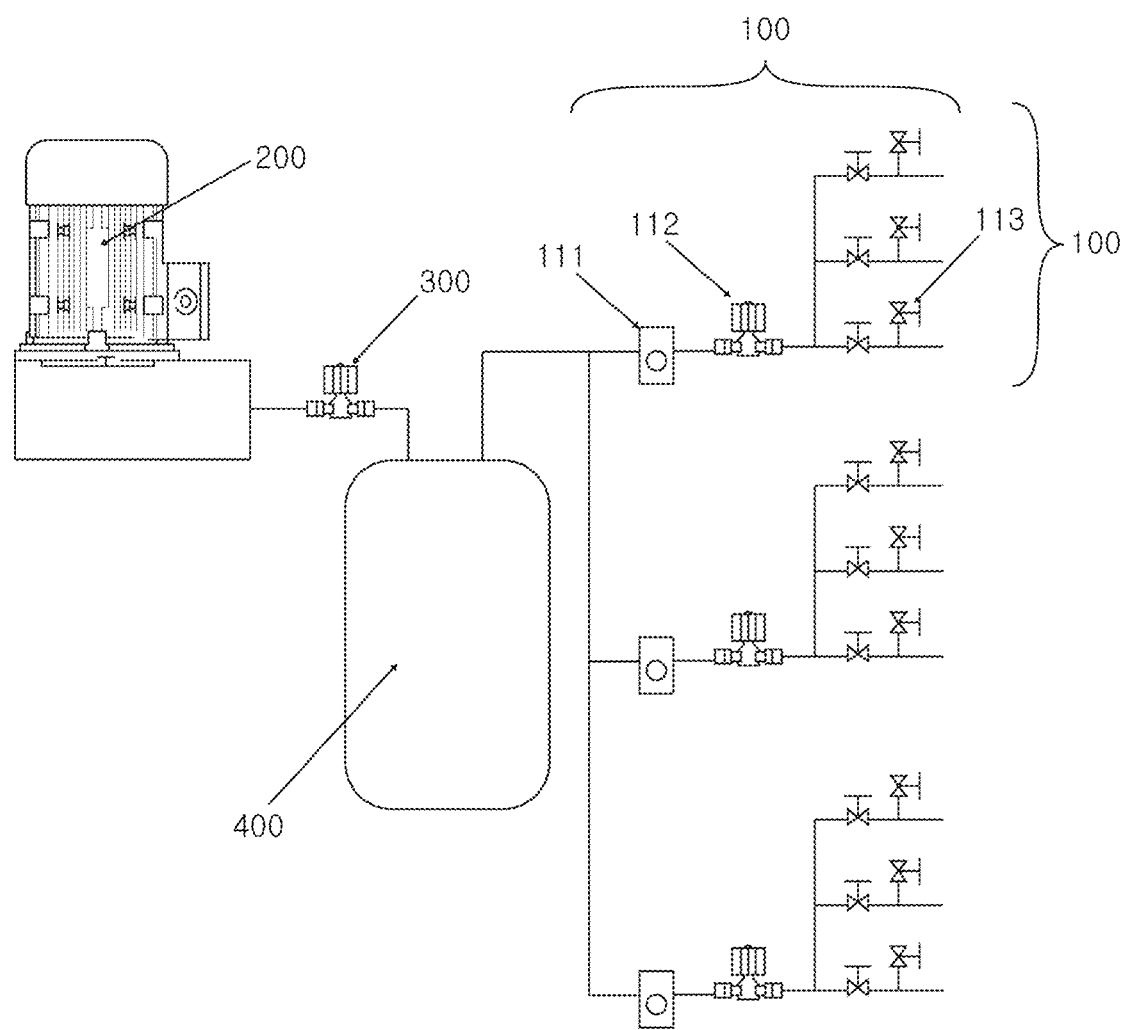
FIG. 10 schematically shows a distribution vacuum controller according to an exemplary embodiment of the present disclosure In the following description, the same or similar elements are labeled with the same or similar reference numbers.

After the glass fibers and the TG were removed through the treatment with DW, the prepared porous microchannels formed of PLGA, i.e., the nerve conduit, was frozen in liquid nitrogen for about 30 seconds, cut to a desired size and then shaped into a desired shape (FIG. 9).

<Example 2> Manufacturing of Porous Nerve Conduit Using Glass Fibers 2

Although vacuum was applied using a syringe in Example 1, a porous nerve conduit was manufactured using a vacuum chamber instead of the syringe for automated pressure control. After the channels were prepared as in Example 1, the upper channels were connected to a vacuum chamber. After setting valves 112, 113 connected to each conduit to OFF, the inside of a vacuum tank 400 was decompressed by operating a vacuum pump 200. Then, the inside of the chamber was decompressed using three vacuum control means 110 connected to a distribution vacuum controller 100. After the decompression was completed, the pressure inside of the chamber was controlled to normal pressure using each vacuum release valve 113. The following procedure was the same as in Example 1.

<Example 3> Investigation of Microstructure Inside Porous Nerve Conduit

The microstructure formed in the microchannels inside the nerve conduit manufactured in Example 1 by dissolving the glass fibers in water was investigated by scanning electron microscopy (SEM) (FIG. 5, FIG. 6 and FIG. 7).

FIG. 5 shows the transverse cross section of the nerve conduit, FIG. 6 shows the magnified SEM images showing the microstructure at the transverse cross section of the nerve conduit and FIG. 7 shows the longitudinal cross section of the nerve conduit. It can be seen that the microchannels were formed continuously inside the nerve conduit from distal to proximal portions and micropores were formed in the microstructure inside the microchannels.

When nerve conduits were manufactured by repeating the method of Example 1 10 times, the size and distribution of the microchannels inside each nerve conduit were not uniform. In contrast, when nerve conduits were manufactured by repeating the method of Example 2 10 times, nerve conduits including microchannels with uniform size and distribution could be produced. It may be because a constant pressure was not applied when the decompression was performed using a syringe in Example 1, whereas the microchannels with uniform size and distribution were distributed inside the nerve conduit when valves and a vacuum chamber were used in Example 2.

The nerve conduit manufactured according to the present disclosure can be manufactured to have various diameters and lengths to be applicable to in vitro and in vivo researches on nerves.

While the present disclosure has been described with reference to the embodiments illustrated in the figures, the embodiments are merely examples, and it will be understood by those skilled in the art that various changes in form and other embodiments equivalent thereto can be performed. Therefore, the technical scope of the disclosure is defined by the technical idea of the appended claims The drawings and the forgoing description gave examples of the present invention. The scope of the present invention, however, is by no means limited by these specific examples. Numerous variations, whether explicitly given in the specification or not, such as differences in structure, dimension, and use of material, are possible. The scope of the invention is at least as broad as given by the following claims.

What is claimed is:

1. An apparatus for manufacturing a porous nerve conduit using glass fibers, comprising:
   a cylindrical container having a bottleneck, the bottleneck forming:
     upper channels, the upper channels configured to accept a plurality of soluble fibers; and
     lower channels, the lower channels having a smaller diameter than the upper channels, the upper and lower channels sloped with a discontinuous angle;
   a polymer material injection means for injecting a polymer material into the container; and
   a vacuum application means for automatically maintaining a constant pressure while applying vacuum to the inside of the container,
   wherein the vacuum application means comprises:
     a vacuum pump connected to a vacuum tank and applies vacuum to the inside of the vacuum tank, the vacuum tank connected to the vacuum pump at one side and the inside of the vacuum tank is maintained at vacuum;
     a distribution vacuum controller;
     a vacuum chamber connected to the distribution vacuum controller and comprises the container and the injection means inside thereof;
     a pressure sensor connected to the vacuum chamber; and a vacuum release valve connected to the vacuum chamber and the distribution vacuum controller, wherein the distribution vacuum controller connects the other side of the vacuum tank to the inside of the vacuum chamber and applies vacuum to the inside of the container, wherein the distribution vacuum controller comprises 1-100 air valve(s), a regulator, and 2-100 vacuum control means comprising 1-100 vacuum release valve(s), wherein the polymer material comprises:
one or more selected from a group consisting of collagen, gelatin, chitosan, alginate, hyaluronic acid, dextran, silk, cellulose, poly-3-hydroxybutyrate (PHB), polyhydroxyvalerate (PHV), poly(hydroxybutyrate-co-valerate) (PHBV), polyorthoester, polyviniy alcohol (PVA), polyethylene glycol (PEG), polyurethane, polyacrylic acid, poly(N-isopropylacrylamide), a poly (ethylene oxide)-poly (propylene oxide)-poly (ethylene oxide) copolymer, poly (dioxanone-b-caprolactone), poly(ε-caprolactone) (PCL), poly(lactic acid) (PLA), poly-L-lactide (PLLA), poly-D-lactide (PDLA), poly-D,L-lactide (PDLLA), poly(glycolic acid) (PGA) or poly(lactic acid-co-glycolic acid) (PLGA) as a polymer; and one or more selected from a group consisting of methylene chloride (dichloromethane, DCM), 1,4-dioxane, chloroform, acetone, anisole, ethyl acetate, methyl acetate, N-methyl-2-pyrrolidone, hexafluoroisopropanol (HFIP), tetrahydrofuran (THF), dimethyl sulfoxide (DMSO), 2-pyrrolidone, triethyl citrate, trifluoroacetic acid (TFA), dimethylformamide (DMF), ethyl lactate, propylene carbonate, benzyl alcohol, benzyl benzoate, Miglyol 810, isopropanol, ethanol, acetonitrile or tetraglycol (TG) as a solvent, wherein microchannels are formed along the axis direction of the nerve conduit as the glass fibers are inserted into the container along the axis direction, wherein micropores are formed in the nerve conduit as the solvent is dissolved in water.

2. The apparatus for manufacturing a porous nerve conduit using glass fibers of claim 1, wherein the container is formed of a transparent material so that the infiltration of the polymer solution can be checked visually.

3. The apparatus for manufacturing a porous nerve conduit using glass fibers of claim 1, wherein the weight/volume % (w/v %) of the polymer and the solvent is 10-40%.

4. The apparatus for manufacturing a porous nerve conduit using glass fibers of claim 1, wherein the polymer material is in a solution state at room temperature.

* * * * *